US012290236B2

(12) United States Patent
Bhowmick et al.

(10) Patent No.: US 12,290,236 B2
(45) Date of Patent: May 6, 2025

(54) MEDICAL DEVICE PLATFORMS AND METHODS OF USING THE SAME

(71) Applicant: Boston Scientific Medical Device Limited, Galway (IE)

(72) Inventors: Nabarun Bhowmick, Kolkata (IN); Deepak Kumar Sharma, Muzaffarnafar (IN); Shrikant Vasant Raut, Mumbai (IN); Subodh Morey, Ponda (IN); Aditya Dhanotiya, Indore (IN)

(73) Assignee: Boston Scientific Medical Device Limited, Galway (IE)

( * ) Notice: Subject to any disclaimer, the term of this patent is extended or adjusted under 35 U.S.C. 154(b) by 519 days.

(21) Appl. No.: 17/221,477

(22) Filed: Apr. 2, 2021

(65) Prior Publication Data

US 2021/0315443 A1 Oct. 14, 2021

Related U.S. Application Data

(60) Provisional application No. 63/007,194, filed on Apr. 8, 2020.

(51) Int. Cl.
*A61B 1/00* (2006.01)
*A61B 1/018* (2006.01)

(52) U.S. Cl.
CPC ...... *A61B 1/00147* (2013.01); *A61B 1/00149* (2013.01); *A61B 1/018* (2013.01)

(58) Field of Classification Search
CPC . A61B 1/00147; A61B 1/00149; A61B 1/018; A61B 2090/508; A61B 2090/571; A61B 90/50
See application file for complete search history.

(56) References Cited

U.S. PATENT DOCUMENTS

2004/0138529 A1* 7/2004 Wiltshire ............ A61B 1/0055
600/144
2012/0118088 A1* 5/2012 Smith ................. A61B 90/57
384/15
(Continued)

FOREIGN PATENT DOCUMENTS

CN 102470003 A 5/2012
JP 2006204372 A 8/2006
(Continued)

OTHER PUBLICATIONS

International Search Report and Written Opinion in International Application No. PCT/IB2021/052789, mailed Jun. 11, 2021 (9 pages).
(Continued)

*Primary Examiner* — John P Leubecker
*Assistant Examiner* — Jae Woo
(74) *Attorney, Agent, or Firm* — Bookoff McAndrews, PLLC

(57) ABSTRACT

A medical device that includes a body and an arm extending from the body and configured to receive a first device such that the first device is suspended relative to the body. Translation of the arm relative to the body is configured to move the first device relative to the body. The medical device includes a receiver extending from the body and configured to receive a second device such that the second device is suspended relative to the body.

15 Claims, 4 Drawing Sheets

(56) References Cited

U.S. PATENT DOCUMENTS

| | | | |
|---|---|---|---|
| 2013/0184691 A1* | 7/2013 | Oskin | A61B 17/00234 606/1 |
| 2014/0163318 A1 | 6/2014 | Swanstrom | |
| 2014/0163327 A1 | 6/2014 | Swanstrom | |
| 2016/0331207 A1* | 11/2016 | Ibrahim | A61M 29/00 |
| 2017/0007345 A1* | 1/2017 | Smith | A61B 1/00042 |
| 2019/0231466 A1 | 8/2019 | Weitzner et al. | |

FOREIGN PATENT DOCUMENTS

| | | |
|---|---|---|
| JP | 2013500788 A | 1/2013 |
| JP | 2016039918 A | 3/2016 |
| WO | 2008070556 A1 | 6/2008 |

OTHER PUBLICATIONS

Khanicheh, A et al., "Endoscope design for the future", Techniques in Gastrointestinal Endoscopy, Jul. 2019, vol. 21, pp. 167-173.

* cited by examiner

MEDICAL DEVICE PLATFORMS AND METHODS OF USING THE SAME

CROSS-REFERENCE TO RELATED APPLICATIONS

This application claims the benefit of priority of U.S. Provisional Patent Application No. 63/007,194, filed Apr. 8, 2020, the entirety of which is incorporated herein by reference.

TECHNICAL FIELD

Various aspects of the disclosure relate generally to medical systems, devices, and related methods. Examples of the disclosure relate to systems, devices, and related methods for positioning and/or controlling one or more medical devices within a subject during a procedure via a handle assembly, among other aspects.

BACKGROUND

Technological developments have given users of medical systems, devices, and methods, the ability to conduct increasingly complex procedures on subjects. One challenge in the field of minimally invasive surgeries such as endoscopy, laparoscopy, and thoracoscopy, among other surgical procedures, is associated with providing control of medical devices during a procedure. Placement of such medical devices within a subject may be difficult. Additionally, actuating various medical systems that control a placement of such medical devices may be counterintuitive or complex to understand. The limitations on medical devices that facilitate access of other devices into a subject for placement may prolong the procedure, limit its effectiveness, and/or cause injury to the subject due to device failure or breakage. There is a need for devices and methods that address one or more of these difficulties or other related problems.

SUMMARY

Aspects of the disclosure relate to, among other things, systems, devices, and methods for accessing a target treatment site with a medical apparatus having intuitive handle assemblies that facilitate positioning of the apparatus, among other aspects. Each of the aspects disclosed herein may include one or more of the features described in connection with any of the other disclosed aspects.

According to an example, a medical device includes a body and an arm extending from the body and configured to receive a first device such that the first device is suspended relative to the body. Translation of the arm relative to the body is configured to move the first device relative to the body. The medical device includes a receiver extending from the body and configured to receive a second device such that the second device is suspended relative to the body.

Any of the medical devices described herein may include any of the following features. The body includes a slot configured to receive the arm such that the arm is movable within the slot. The body includes a locking mechanism engaged with the arm and configured to fix the arm at one of a plurality of positions relative to the body. The arm is configured to move laterally relative to the body in one or more lateral directions. The arm is movable independent of the receiver such that the first device is movable relative to the second device. At least a portion of the arm is transparent such that a lumen of the arm is visible to allow visualization of the first device within the lumen of the arm. The arm is configured to pivot relative to the body in one or more pivotable directions. The arm includes an inlet opening and an outlet opening sized and shaped to receive the first device. The inlet opening is positioned proximally relative to the outlet opening and is configured to form a seal against the first device. The outlet opening is positioned adjacent to the receiver and is configured to permit the first device to extend outwardly from the arm and toward the second device. The arm is configured to allow axial translation of the first device relative to the outlet opening when the first device is secured to the arm at the inlet opening. The medical device further including a second body that is configured to engage an ancillary surface. The second body includes one or more rails and the body includes one or more wheels movably coupled to the one or more rails of the second body such that the body is movable relative to the second body. The arm and the receiver are movable relative to the second body in response to translation of the one or more wheels of the body along the one or more rails. The arm is movable with the receiver such that the first device and the second device are movable relative to the second body.

According to another example, a medical device includes a platform having a body defined by a proximal end and a distal end. The medical device includes an arm movably coupled to the body and configured to suspend a first device relative to the ancillary surface. The first device is movable between the proximal end and the distal end in response to translation of the arm along the body. The medical device includes a receiver at the distal end of the body and configured to suspend a second device relative to the ancillary surface. The second device is fixed at the distal end.

Any of the medical devices described herein may include any of the following features. The arm is movable independent of the receiver such that the first device is movable relative to the second device. The arm includes an inlet opening and an outlet opening sized and shaped to receive the first device. The inlet opening is configured to form a seal against the first device, and the outlet opening is configured to permit the first device to extend outwardly from the arm and toward the second device. The arm is configured to allow axial translation of the first device relative to the outlet opening when the first device is secured to the arm at the inlet opening. The medical device further includes a second body that is configured to engage an ancillary surface. The body includes a pair of wheels movably coupled to a pair of rails of the second body such that the body is movable relative to the second body. The arm and the receiver are movable relative to the second body in response to translation of the pair of wheels along the pair of rails.

According to another example, a medical device includes a fixed body, a movable body coupled to and movable relative to the fixed body, and an arm extending from the movable body and configured to receive a first device. The first device is movable relative to the fixed body in response to translation of the arm and the movable body relative to the fixed body. The medical device includes a receiver extending from the movable body and configured to receive a second device. The arm and the receiver are movable relative to the fixed body in response to translation of the movable body along the fixed body.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

DETAILED DESCRIPTION

Figure 1:
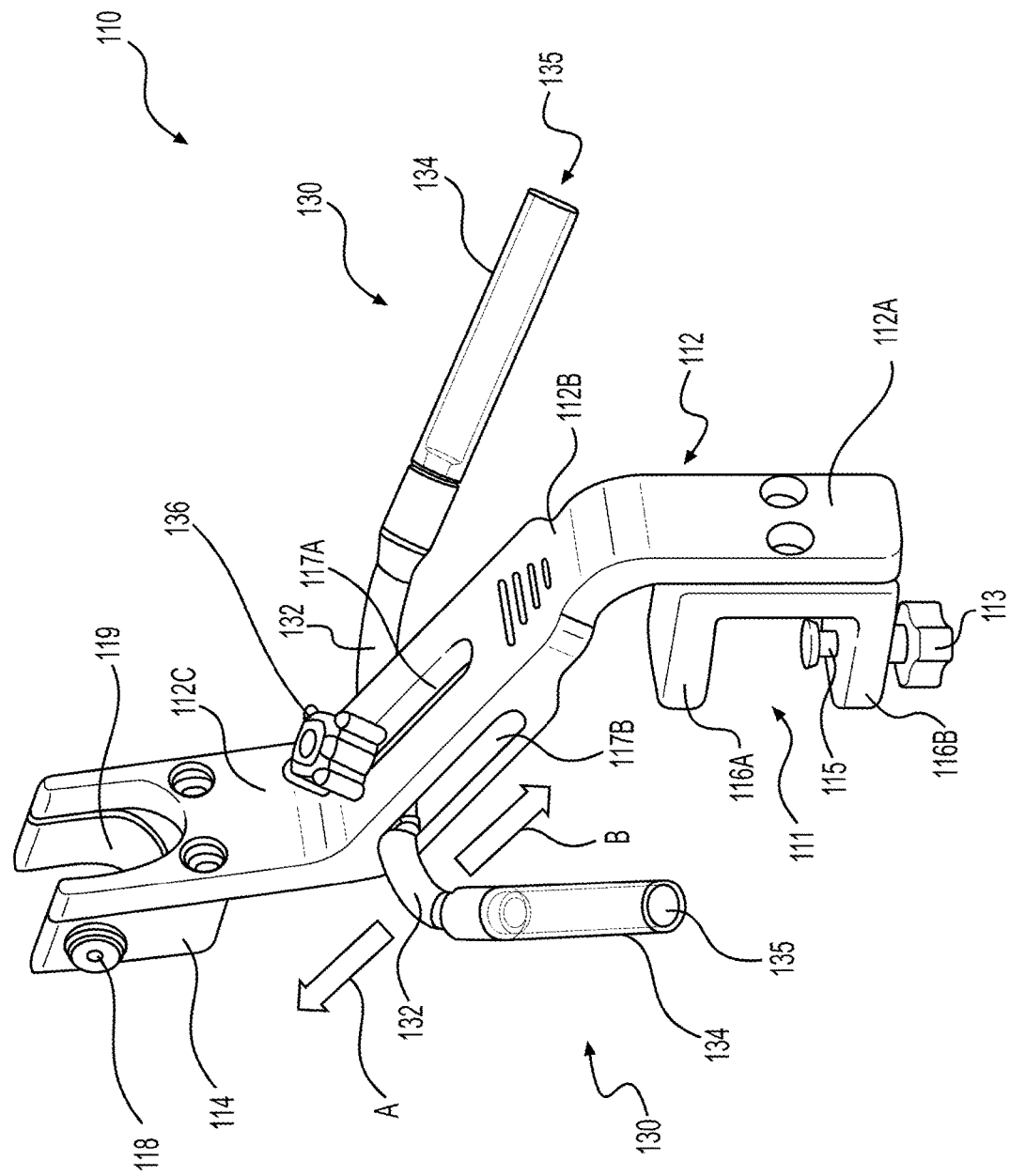
FIG. 1 is a perspective view of an exemplary medical device including a platform, according to aspects of this disclosure.

Examples of the disclosure include systems, devices, and methods for controlling multiple components of a medical instrument at a target site within the body, where the components generally require manipulation to access a target site, among other aspects. Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., a patient). By contrast, the term "proximal" refers to a portion closest to the user when placing the device into the subject. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure may be used to facilitate a control and positioning of tools/devices (e.g., end effector) of a medical instrument at a target treatment site by providing one or more mechanisms and/or assemblies for positioning said tools/devices at the target treatment site. For instance, some examples combine a platform with a medical instrument and one or more medical devices to facilitate selective control, positioning, and/or manipulation of components of the medical instrument, such as, for example, an end effector. The platform may include a body configured to suspend the medical instrument and the one or more medical devices relative to an ancillary structure, such as, for example, a table. The platform may include movable arms that may be selectively adjustable relative to the body of the platform for positioning the one or more medical devices at a plurality of positions and/or orientations relative to the medical instrument and the target site.

Examples of the disclosure may relate to devices and methods for performing various medical procedures and/or treating portions of the large intestine (colon), small intestine, cecum, esophagus, any other portion of the gastrointestinal tract, and/or any other suitable subject (e.g., patient) anatomy (collectively referred to herein as a "target treatment site"). The device and related methods may be used laparoscopically or endoscopically, or in any other open or minimally invasive procedure, including thorascopic and ENT procedures. Reference will now be made in detail to examples of this disclosure described above and illustrated in the accompanying drawings. Wherever possible, the same reference numbers will be used throughout the drawings to refer to the same or like parts.

FIG. 1 shows a schematic depiction of an exemplary medical device 110 in accordance with an example of this disclosure. The medical device 110 may include a platform 112 having a body defined by a proximal body 112A, an intermediate body 112B, and a distal body 112C. In the example, the intermediate body 112B may extend between the proximal body 112A and the distal body 112C such that the proximal body 112A and the distal body 112C are separated from one another by the intermediate body 112B disposed therebetween. The intermediate body 112B may include various suitable sizes, shapes, and/or configurations relative to the proximal body 112A and the distal body 122C. For example, the intermediate body 112B may be configured to form an angle between the proximal body 112A and/or the distal body 112C that positions a first device received along the proximal body 112A (see FIG. 3) at an ergonomic position relative to a second device received along the intermediate body 112B and/or the distal body 112C. Further, the proximal body 112A and/or the distal body 112C may each include a longitudinal length that is aligned and/or oriented at least partially transverse to a longitudinal length of the intermediate body 112B. In some embodiments, the proximal body 112A and/or the distal body 112C may include a longitudinal length that is relatively parallel to one another.

It should be understood that the intermediate body 112B of the platform 112 may extend relatively above and/or be suspended by the proximal body 112A. Further, the distal body 112C of the platform 112 may extend relatively above and/or be suspended by the intermediate body 112B. In this instance, the proximal body 112A of the platform 112 may provide a base support for the platform 112. It should be appreciated that the platform 112 may include additional and/or fewer bodies 112A, 112B, 112C than those shown and described herein without departing from a scope of the disclosure. Additionally and/or alternatively, in other embodiments, the body of the platform 112 may include various other suitable shapes, sizes, and/or configurations than those shown and described herein.

Still referring to FIG. 1, in some embodiments, the body of the platform 112 may be a unitary structure such that the proximal body 112A, the intermediate body 112B, and the distal body 112C may be integrally formed. In other embodiments, the body of the platform 112 may be separate components secured to one another to form the body. The proximal body 112A of the platform 112 may be configured and operable to secure the platform 112 to an ancillary device and/or structure, such as, for example, a table or bed (not shown). Such ancillary body/structure may be fixed relative to the patient. For example, the proximal body 112A of the platform 112 may include a clamp mechanism 111 configured and operable to secure the platform 112 to an ancillary device and/or structure. The clamp mechanism 111 may include a pair of jaws 116A, 116B that are sized and shaped to receive the ancillary device and/or structure therebetween.

The intermediate body 112B of the platform 112 may include one or more slots 117A, 117B formed along a longitudinal length of the intermediate body 112B. For example, the intermediate body 112B may include a top slot 117A formed through a top wall of the intermediate body 112B and extending between the opposing terminal ends of the intermediate body 112B (e.g., between the proximal body 112A and the distal body 112C). Further, the intermediate body 112B may include one or more side slots 117B formed through a sidewall of the intermediate body 112B and extending between the opposing terminal ends of the intermediate body 112B (e.g., between the proximal body 112A and the distal body 112C). In an example, the intermediate body 112B includes two slots 117B on opposite sides of the intermediate body 112B.

Still referring to FIG. 1, the platform 112 may further include one or more movable arms 130 movably coupled to the intermediate body 112B. In the example, the platform 112 includes a pair of movable arms 130 extending laterally outward from the intermediate body 112B via the one or more side slots 117B. The pair of movable arms 130 may be securely coupled to the intermediate body 112B by a locking mechanism 136 received through the top slot 117A. In this instance, with the pair of movable arms 130 received within the intermediate body 112B via the side slots 117B and the locking mechanism 136 received within the intermediate body 112B via the top slot 117A, the locking mechanism 136 may be configured to engage the pair of movable arms 130 within the intermediate body 112B.

The locking mechanism 136 may be further configured to allow movement of the pair of movable arms 130 relative to the body of the platform 112 in response to actuating the locking mechanism 136. For example, the locking mechanism 136 may be configured such that actuation of the locking mechanism 136 may unlock the pair of movable arms 130 from the intermediate body 112B to thereby allow movement (e.g., translation) of the pair of movable arms 130 in one or more directions (e.g., a distal direction A, a proximal direction B, side-to-side, etc.) relative to the platform 112. In some embodiments, the movable arms 130 may be configured to pivot and/or rotate within the side slots 117B and/or relative to the intermediate body 112B (e.g., bout an axis extending through both the side slots 117B) in response to actuation of the locking mechanism 136. In embodiments, the locking mechanism 136 may include a rotatable actuator (e.g., a nut, a screw, a knob, etc.) that is rotatable (e.g., clockwise, counter clockwise, etc.) relative to the intermediate body 112B.

Still referring to FIG. 1, each of the pair of movable arms 130 may include a curved portion 132 and/or a linear portion 134, with the curved portion 132 coupled to the intermediate body 112B via the locking mechanism 136. Further, the linear portion 134 of the movable arm 130 may extend proximally from the curved portion 132. It should be understood that the curved portion 132 of the movable arm 130 may include a longitudinal length having a predefined curvature between opposing terminal ends of the curved portion 132. Further, the curved portion 132 of the movable arm 130 may have a configuration to extend the linear portion 134 laterally outward from the intermediate body 112B and/or proximally relative to the body. Accordingly, the curved portion 132 may be sized and shaped to suspend the linear portion 134 relative to the body of the platform 112.

In some embodiments, the curved portion 132 may be flexibly bendable such that a configuration (e.g., size, shape, profile, etc.) of the curved portion 132 may be adjustable in response to an application of force thereto. In this instance, a position of the linear portion 134 relative to the body of the platform 112 may be selectively adjustable. In other embodiments, the curved portion 132 may be omitted entirely such that the linear portion 134 may be coupled to the intermediate body 112B, thereby providing an alternative configuration of the movable arms 130 relative to the platform 112. Alternatively, the linear portion 134 may be excluded such that the movable arms 130 may include a continuously curved configuration.

The linear portion 134 of the movable arm 130 may include an inlet 135 at a terminal end of the linear portion 134. As described in further detail herein, the inlet 135 may define an opening that is sized and shaped to receive a device (e.g., FIG. 3, a device 140) into the movable arm 130. It should be appreciated that the curved portion 132 and the linear portion 134 of the movable arm 130 may include a configuration that positions the inlet 135 for force proximally toward a location of a user of the medical device 110.

Still referring to FIG. 1, the portions 132, 134 of the movable arms 130 may be sized and shaped to form a predefined gap between the inlets 135 to provide ample working space and/or clearance for a user of the medical device 110 to control one or more devices (e.g., FIG. 3, the devices 140) coupled to the movable arms 130 during a procedure. In other words, a curvature and length of the curved portion 132 of the movable arm 130, and a length of the linear portion 134, may be operable to diverge the pair of movable arms 130 outwardly relative to the intermediate body 112B and/or to one another. The platform 112 may be configured and operable to facilitate operation of multiple instruments (e.g., the devices 140) by at least a single user, thereby improving a control, articulation, and/or dexterity of the instruments by the user.

In the example, the curved portion 132 of one or more of the movable arms 130 may be formed of an opaque metal and/or plastic, and the linear portions 134 of one or more of the movable arms 130 may be formed of a transparent plastic. In this instance, with the linear portion 134 being transparent, the movable arm 130 may be operable to facilitate a visualization of one or more devices received within the linear portion 134 via the inlet 135. In other embodiments, the portions 132, 134 of the movable arms 130 may include various other suitable characteristics and/or configurations (e.g., opacity, transparency, sizes, shapes, etc.) without departing from a scope of this disclosure.

Still referring to FIG. 1, the distal body 112C of the platform 112 may be configured and operable to hold and/or suspend one or more instruments and/or devices on the platform 112. For example, the distal body 112C of the platform 112 may include a receiver 114 configured to hold an instrument therein. In the example, the receiver 114 of the distal body 112C may include a channel 119 that is sized and shaped in accordance with a profile (e.g., a width, cross-sectional dimension, diameter, etc.) of an instrument (e.g., FIG. 3, a medical instrument 120) to facilitate suspending the instrument on the platform 112 and relative to one or more ancillary structures (e.g., a table, a bed, etc.). For example, the channel 119 may be U-shaped to receive a cylindrically-shaped profile of the medical instrument 120. It should be appreciated that the channel 119 of the receiver 114 may include a longitudinal length (measured in a proximal to distal direction) sufficient for maintaining the instrument at a fixed orientation when received therein such that the instrument may be stabilized along the platform 112 during a procedure.

The platform 112 may further include a fastener 118 on the distal body 112C that may be configured to securely engage an instrument to the receiver 114 when received within the channel 119. In the example, the fastener 118 may include a nut, a screw, a knob, a button, a lever, a switch, and/or the like. In some embodiments, the fastener 118 may be biased into the channel 119 of the receiver 114 (via a spring, for example) such that the fastener 118 is configured to form a snap-fit connection with an instrument (e.g., FIG. 3, a medical instrument 120) received within the channel 119. In this instance, the receiver 114 of the platform 112 may be configured to facilitate a relatively quick connection and disconnection of an instrument to the channel 119.

Figure 2:
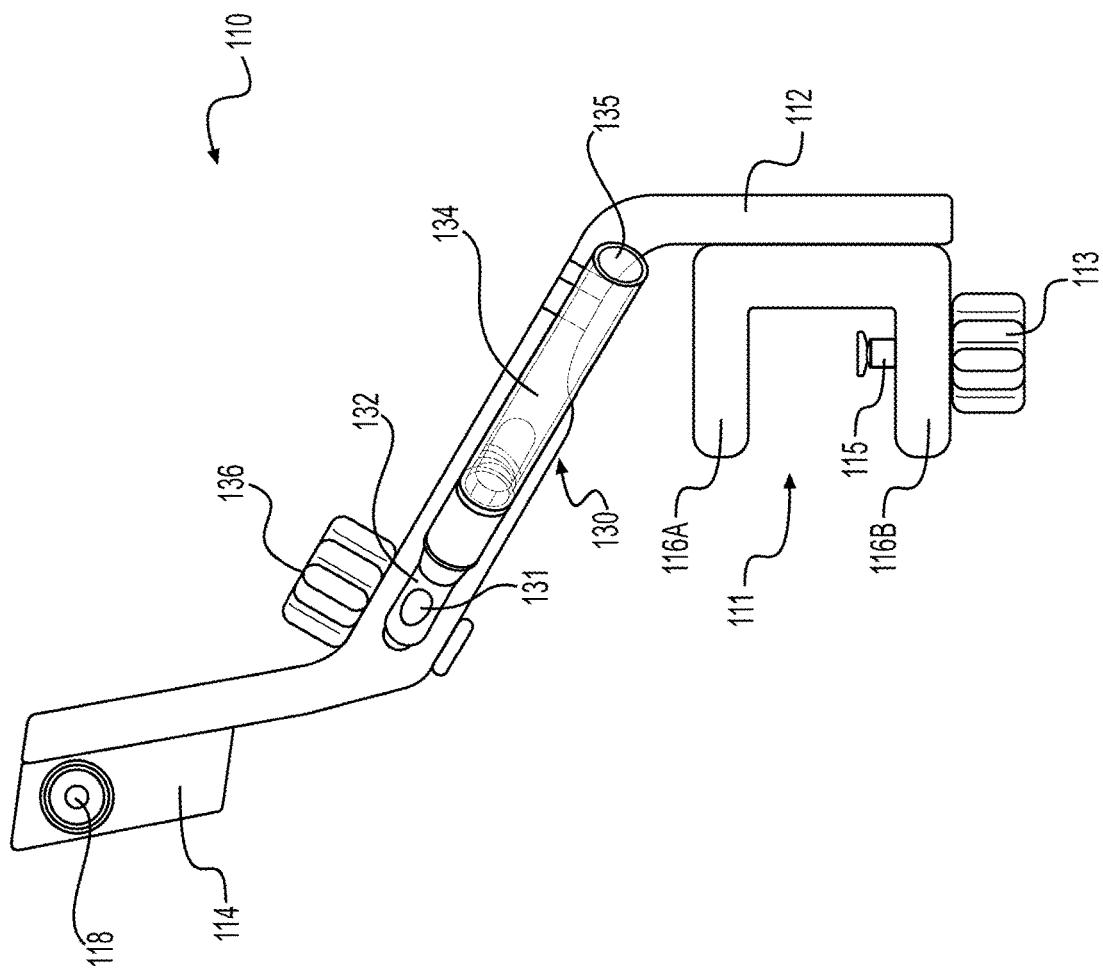
FIG. 2 is a side view of the medical device of FIG. 1, according to aspects of this disclosure.

Referring now to FIG. 2, the curved portion 132 of the movable arm 130 may include an outlet 131 (e.g., an aperture) positioned along a longitudinal length of the curved portion 132. The outlet 131 of the curved portion 132 may be sized, shaped, and configured to receive one or more components of a device therethrough, such as, for example, of a device coupled to the movable arm 130 at the linear portion 134. Additionally, as briefly described above, the clamp mechanism 111 of the platform 112 may include a pair of jaws 116A, 116B coupled to the proximal body 112A. In the example, the pair of jaws 116A, 116B of the clamp mechanism 111 are fixed relative to one another. Further, the clamp mechanism 111 may include a movable brace 115 disposed through at least one of the pair of jaws 116A, 116B.

For example, the bottom jaw 116B of the clamp mechanism 111 may include an actuator 113 coupled to the movable brace 115, with the movable brace 115 extending through the bottom jaw 116B and disposed between the pair of jaws 116A, 116B. In this instance, actuation (e.g., rotation) of the actuator 113 may provide movement (e.g., translation) of the movable brace 115 relative to the pair of jaws 116A, 116B, such as, for example, toward the jaw 116A. Accordingly, the clamp mechanism 111 may be configured and operable to secure an ancillary device and/or structure to the platform 112 in response to positioning the ancillary device between the pair of jaws 116A, 116B and actuating the actuator 113 to thereby engage the movable brace 115 against the ancillary device.

Figure 3:
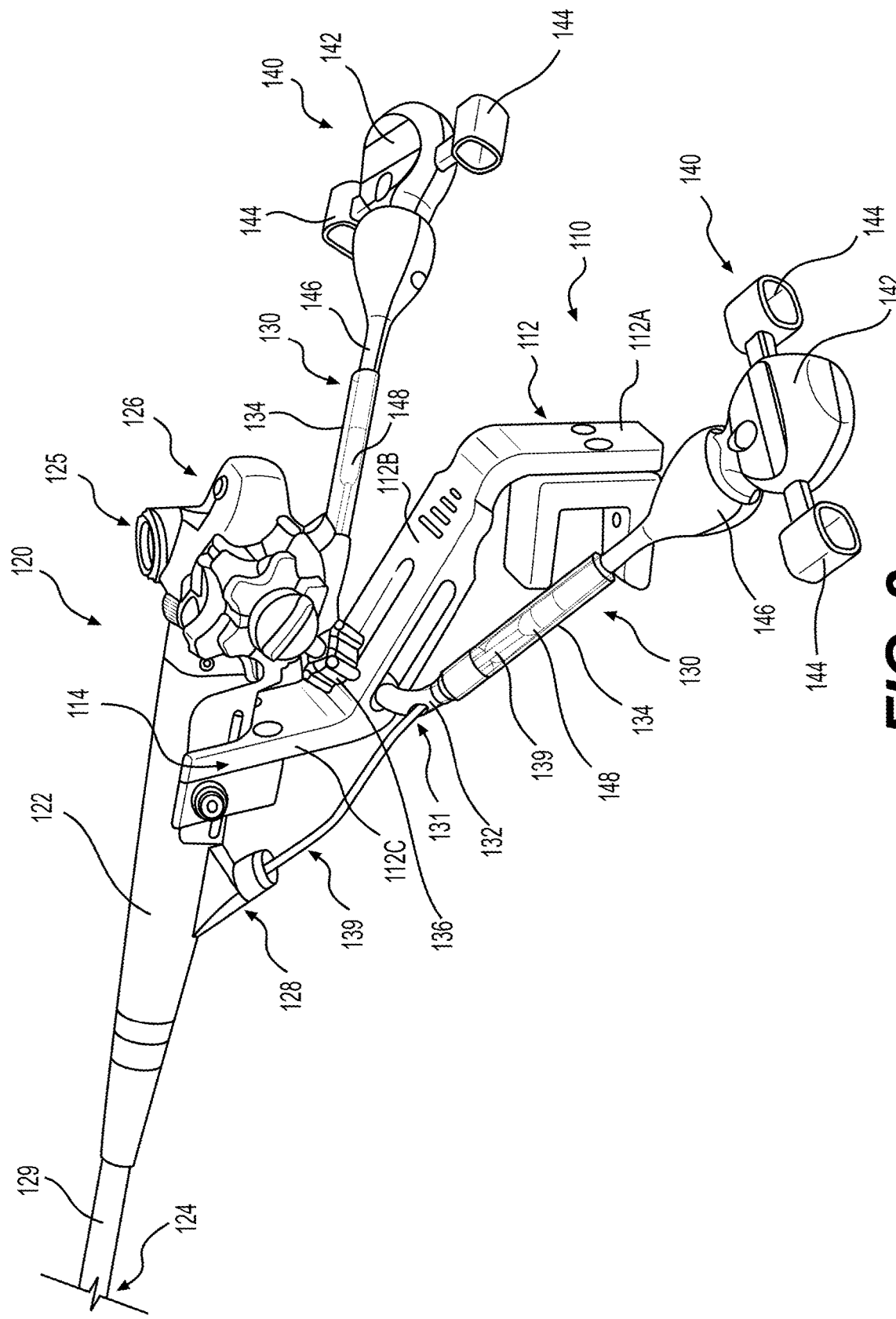
FIG. 3 is a perspective view of the medical device of FIG. 1 suspending one or more medical devices on the platform, according to aspects of this disclosure.

Referring now to FIG. 3, an exemplary method of using the medical device 110 to suspend and/or hold one or more devices and/or instruments is schematically depicted. For example, the platform 112 of the medical device 110 may be configured and operable to support a medical instrument 120. The medical instrument 120 is configured to receive and facilitate positioning of one or more components relative to a subject (e.g., a patient). In the example, a handle 122 of the medical instrument 120 may be disposed within the channel 119 (FIG. 1) of the receiver 114 and securely coupled thereto by actuating the fastener 118. Accordingly, the medical instrument 120 may be suspended by the distal body 112C of the platform 112 relative to a subject, a user of the medical device 110 and/or the medical instrument 120, and/or an ancillary structure (not shown) that the platform 112 may be secured to (e.g., via the clamp mechanism 111). The platform 112 of the medical device 110 may provide control of the medical instrument 120 while minimizing a necessity to manually grasp, hold, maneuver, and/or actuate the medical instrument 120.

By way of illustrative example, the medical instrument 120 may be any type of endoscope, duodenoscope, gastroscope, colonoscope, ureteroscope, bronchoscope, catheter, or other delivery system. For example, the medical instrument 120 may include the handle 122, a distal end 124, a proximal end 126, and one or more ports 128. The handle 122 of the medical instrument 120 may have one or more lumens (not shown) that communicate with one or more other devices coupled thereto, such as, for example, one or devices 140. The handle 122 may further include the one or more ports 128 that open into the one or more lumens of the handle 122. As described in further detail herein, the one or more ports 128 may be sized and shaped to receive one or more instruments therethrough, such as, for example, the one or more devices 140.

Still referring to FIG. 3, the distal end 124 of the medical instrument 120 may include a shaft 129 extending outwardly therefrom. The shaft 129 of the medical instrument 120 may include a tube that is sufficiently flexible such that the shaft 129 is configured to selectively bend, rotate, and/or twist when being inserted into and/or through a subject's tortuous anatomy. The shaft 129 may have one or more lumens (not shown) extending therethrough that include, for example, a working lumen for receiving instruments (e.g., the one or more devices 140). In other examples, the shaft 129 may include additional lumens such as a control wire lumen for receiving one or more control wires for actuating one or more distal parts/tools (e.g., an articulation joint, an elevator, etc.), a fluid lumen for delivering a fluid, an illumination lumen for receiving at least a portion of an illumination assembly (not shown), and/or an imaging lumen for receiving at least a portion of an imaging assembly (not shown).

The proximal end 126 of the medical instrument 120 may include one or more actuation mechanisms (e.g., knobs, buttons, levers, switches, and/or other suitable actuators) configured to control at least one of deflection of the shaft 129 (e.g., through actuation of a control wire), delivery of a fluid, emission of illumination, and/or various imaging functions. The proximal end 126 of the medical instrument 120 may further include a device port 125 that is configured and operable to receive one or more components of the medical instrument 120, such as, for example, an umbilicus (not shown) for connecting devices to the medical instrument 120 (e.g., imaging devices).

Still referring to FIG. 3, the platform 112 of the medical device 110 may be configured and operable to support one or more devices 140 via the one or more movable arms 130. In the example, each of the one or more devices 140 may include a body 142, one or more actuators 144, a shaft 146, and a tip 148. In the example, a lumen of the linear portion 134 may be sized and shaped in accordance with a profile of the shaft 146 and/or the tip 148 of the device 140. The linear portion 134 is configured and operable to form a seal against an exterior surface of the shaft 146 and/or the tip 148 of the device 140 when received therein via the inlet 135. For example, the movable arm 130 may be configured to provide a friction fit between the linear portion 134 and the shaft 146. The linear portion 134 of the movable arm 130 may securely fasten the device 140 to the platform 112. The linear portion 134 may be of a suitable compressible material to permit insertion of the shaft 146 having various sizes and/or shapes. In other embodiments, each of the movable arms 130 may include a fastener mechanism (e.g., similar to the fastener 118) along the curved portion 132 and/or the linear portion 134 for securely engaging the device 140 therein.

In the example, the linear portion 134 of the movable arm 130 may be further sized, shaped, and configured to permit axial translation of the shaft 146 and/or the tip 148 of the device 140 therethrough. Each of the movable arms 130 may provide for linear movement of the shaft 146 and the tip 148 within a lumen of the linear portion 134 in response to actuation of the body 142 of the device 140 by a user. Additionally and/or alternatively, the linear portion 134 of the movable arm 130 may be further sized, shaped, and configured to permit rotation of the shaft 146 and/or the tip 148 of the device 140 within the linear portion 134, about a longitudinal axis of the linear portion 134 and the shaft 146. In other embodiments, the linear portion 134 may be configured and operable to rotate with the device 140 coupled thereto relative to the curved portion 132 of the movable arm 130. In these instances, the movable arm 130 may provide increased control, dexterity, and/or degrees of freedom for moving the devices 140 relative to the platform 112 and/or a subject during a procedure. Examples of the devices 140 are described in U.S. App. No. 62/987,694, entitled "Medical Device Handle Assemblies and Methods of Using the Same," filed on Mar. 10, 2020, the disclosure of which is incorporated by reference herein.

In some embodiments, the device 140 may further include a conduit 139 extending distally from the tip 148 such that the conduit 139 is received within the movable arm 130. The conduit 139 may be in fluid communication with the body 142 of the device 140 and may be coupled to the shaft 129 of the medical instrument 120 for controlling one or more components at a target treatment site in a subject. The linear portion 134 of the movable arm 130 may be operable to facilitate an alignment of the conduit 139 with the outlet 131 of the curved portion 132 via the transparent configuration of the linear portion 134. A transparency of the linear portion 134 may allow a user of the medical device 110 to visually guide the conduit 139 toward the outlet 131 of the curved portion 132 when the conduit 139 is disposed within the linear portion 134.

Still referring to FIG. 3, in some embodiments, the outlet 131 may positioned along a region of the curved portion 132 adjacent to and/or facing toward the port 128 of the medical instrument 120 to facilitate connection of the conduit 139 from the movable arm 130 to the medical instrument 120. Accordingly, with the conduit 139 of the device 140 extending outwardly from the movable arm 130 via the outlet 131, the conduit 139 may be received within the port 128 of the medical instrument 120. In some examples, a position and/or orientation of the movable arms 130 relative to the body of the platform 112 may be modified during a procedure in response to unlocking the locking mechanism 136. In this instance, the movable arms 130 may be selectively adjusted by moving the curved portions 132 of the movable arms 130 through and along the side slots 117B of the intermediate body 112B.

It should be understood that the locking mechanism 136 may be operable to move along the top slot 117A of the intermediate body 112B in response to movement of the curved portion 132 along the side slot 117B. For example, the movable arms 130 may be translated toward the proximal body 112A and away from the distal body 112C, and vice versa. Further, the movable arms 130 may be moved side-to-side (e.g., transverse to a proximal-distal direction) relative to the intermediate body 112B such that at least one of the devices 140 received in one of the pair of movable arms 130 is moved proximally and another device 140 received in the other pair of movable arms 130 is moved distally. By way of further example, the movable arms 130 may be moved vertically (e.g., in an upward and downward direction) in response to pivotal movement of the movable arms 130 about an axis extending through the pair of side slots 117B. In the example, the locking mechanism 136 may allow the movable arms 130 to move to a plurality of positions along the side slots 117B and relative to the intermediate body 112B.

Still referring to FIG. 3, it should be understood that the curved portion 132 and/or the linear portion 134 of the movable arm 130 may include various other sizes and/or shapes in accordance with a profile of other suitable devices 140 for coupling to the platform 112. It should also be understood that the channel 119 of the receiver 114 may be sized and/or shaped with various other suitable configurations in accordance with a profile of other suitable medical instruments 120 for coupling to the platform 112. With the medical instrument 120 suspended by the platform 112 of the medical device 110, a user may actuate the one or more components of the medical instrument 120 without requiring continuous, manual control of the handle 112 during a procedure.

Furthermore, by maintaining the one or more devices 140 in a suspended state relative to a subject, a user may selectively grasp, actuate, and release the one or more devices 140 during a procedure without requiring continuous, manual control of the devices 140. In this instance, a user of the devices 140 may have greater flexibility and freedom for performing the procedure on the subject. By securing the platform 112 of the medical device 110 to an ancillary surface and/or device, such as, for example, a table 10 (FIG. 4), the platform 112 may retain the one or more medical instruments 120 and/or devices 140 along the body of the platform 112 in a secured and stable position relative to a subject without necessitating physical control of said instruments 120 and/or devices 140 by a hand of the user.

Figure 4:
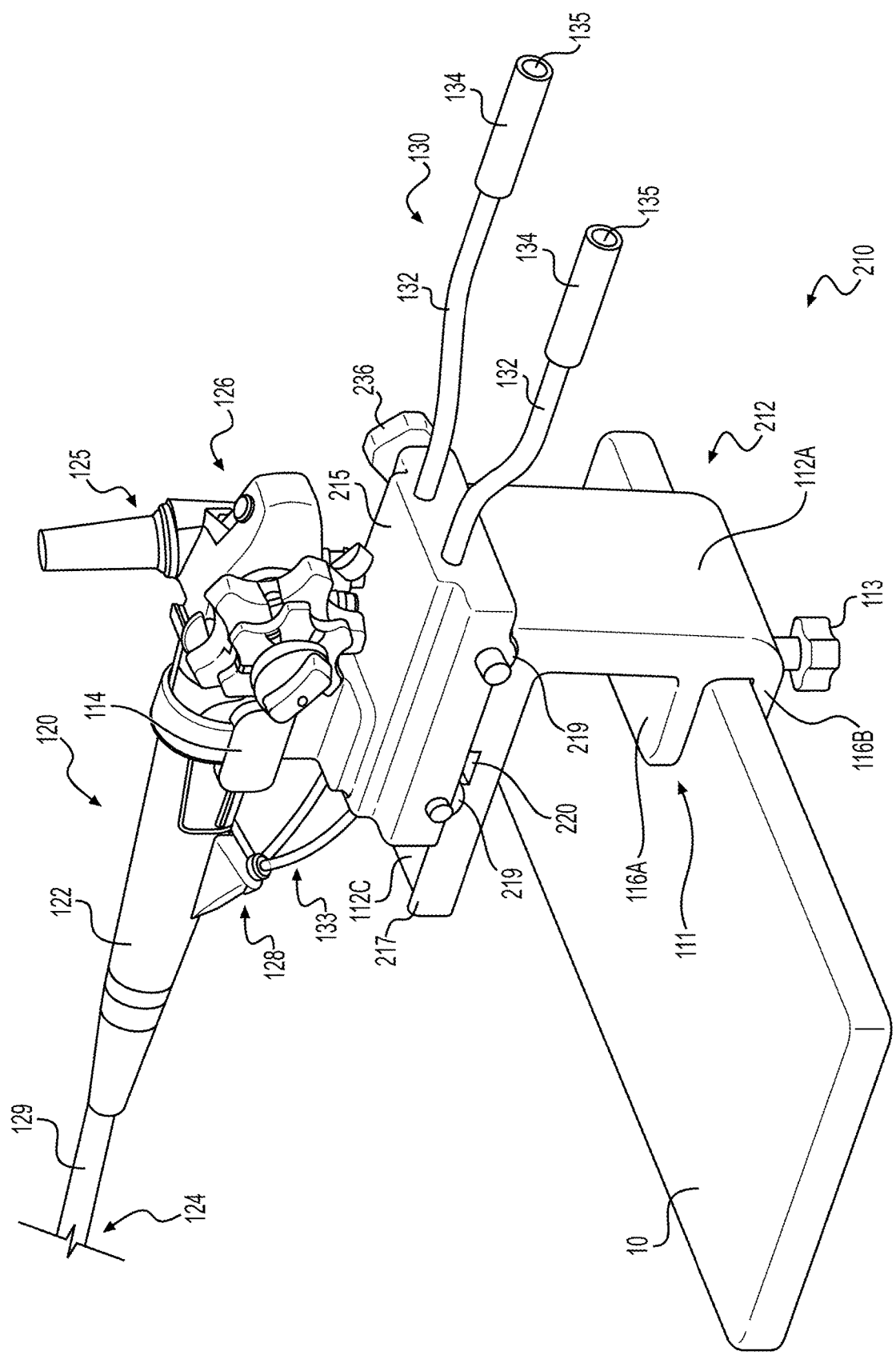
FIG. 4 is a perspective view of another exemplary medical device including a platform for suspending one or more medical devices, according to aspects of this disclosure.

FIG. 4 shows a schematic depiction of another exemplary medical device 210 in accordance with an example of this disclosure. Except as otherwise described below, the medical device 210 may be substantially similar to the medical device 110 described above such that like reference numerals are used to identify like components. It should be understood that the medical device 210 may be configured and operable like the medical device 110 and that the medical device 210 may be readily incorporated with the one or more medical instruments 120 and/or devices 140 described above.

For example, the medical device 210 may include a platform 212 having a defined by a proximal body 112A and a distal body 112C. In this instance, the distal body 112C extends transversely relative to the proximal body 112A and extends distally from a top portion/end of the proximal body 112A. The proximal body 112A may include the clamp mechanism 111 along a bottom portion of the proximal body 112A for securing the medical device 210 to an ancillary structure and/or device, such as, for example, a table 10. In this instance, the table 10 is received between the pair of jaws 116A, 116B and secured therein by actuating the actuator 113 to engage the movable brace 115 (FIG. 2) against a bottom surface of the table 10.

Still referring to FIG. 4, the distal body 112C may include one or more rails 217 disposed along a top surface of the distal body 112C. In the example, the distal body 112C includes a pair of rails 217 on the top surface and positioned along the lateral sides of the distal body 112C. In this instance, the pair of rails 217 may extend along all and/or substantially all of a longitudinal length of the distal body 112C. The distal body 112C of the platform 212 may include further one or more recesses 220 disposed along a portion of the pair of rails 217. In the example, each of the rails 217 may include the recess 220 along an intermediate portion of the rail 217; however, it should be understood that additional and/or fewer recesses 220 may be included along various other portions of the rails 217 than those shown and described herein.

As described in further detail herein, the pair of rails 217 may be configured to receive one or more other components of the medical device 210 therein, such as, for example, a wheel 219. Further, the one or more recesses 220 along the rails 217 may be configured to secure a position of the one or more components of the medical device 210 (e.g., a wheel) to the rail 217 when received within the recess 220. The medical device 210 may further include a movable platform 215 coupled to the distal body 112C of the platform 112. In the example, the movable platform 215 of the medical device 210 may include one or more wheels 219 positioned along a bottom surface of the movable platform 215.

For example, the movable platform 215 may include a pair of wheels 219 along each lateral side of the movable platform 215, with the pair of wheels 219 configured and operable to engage the pair of rails 217 on the distal body 112C. In this instance, with the wheels 219 of the movable platform 215 coupled to the pair of rails 217 of the distal body 112C, the movable platform 215 may be configured to translate along the platform 112 (proximal to distal, and vice versa) to reposition one or more devices received on the mobile platform 215 relative to the platform 112, such as, for example, the medical instrument 120 and/or the devices 140 (FIG. 3). The one or more recesses 220 along the pair of rails 217 may engage the wheels 219 when received therein, thereby inhibiting movement of the movable platform 215 relative to the distal body 112C of the platform 212, in the absence of a proximally, or distally, directed force on the movable platform 215.

Still referring to FIG. 4, the movable platform 215 may include a locking mechanism 236 that may be configured to selectively permit and inhibit movement of the movable platform 215 relative to the distal body 112C of the platform 212. In some embodiments, the locking mechanism 236 may be operable to lock the wheels 219 of the movable platform 215 upon actuating the locking mechanism 236, thereby inhibiting rotation of the wheels 219 along the rails 217 of the distal body 112C. In other embodiments, the locking mechanism 236 may be operable to engage the rails 217 with a movable lever and/or brace (not shown) positioned along a bottom surface of the movable platform 215 upon actuating the locking mechanism 236, thereby inhibiting translation of the movable platform 215 relative to the platform 212.

The movable platform 215 of the medical device 210 may include the pair of movable arms 130 extending proximally from a body of the movable platform 215. The movable arms 130 of the medical device 210 may include the curved portions 132, the linear portions 134, and the inlets 135 described in detail above. Accordingly, the movable arms 130 of the medical device 210 may be configured and operable to receive one or more devices 140 (FIG. 3) through the inlets 135 and into the portions 132, 134 of the movable arms 130. The movable platform 215 of the medical device 210 may further include the receiver 114 positioned along a top surface of the movable platform 215. The receiver 114 may be sized, shaped, and configured to receive one or more instruments therein, such as, for example, the medical instrument 120 described above.

Still referring to FIG. 4, the movable platform 215 may include a pair of flexible tubes 133 extending outwardly from a distal surface of the movable platform 215, opposite of a proximal surface including the curved portions 132 of the movable arms 130 thereon. With the medical instrument 120 coupled to the medical device 210 at the receiver 114, the pair of flexible tubes 133 may be coupled to the ports 128 on the handle 122. In this instance, the pair of flexible tubes 133 may be in communication with one or more lumens of the medical instrument 120 via the ports 128.

In the example, each of the pair of flexible tubes 133 may define a lumen that is in communication with a lumen of the curved portion 132 and the linear portion 134 of the movable arms 130. Further, the movable platform 215 may include one or more lumen (not shown) that fluidly connect the lumen of the curved portion 132 to the lumen of the flexible tube 133. Accordingly, it should be appreciated that one or more components of the devices 140 coupled to the movable arms 130 may extend through the pair of flexible tubes 133 and be received in the medical instrument 120 via the port 128, such as, for example, the conduits 139 (FIG. 3). Further, with the curved portion 132 and the linear portion 134 of the movable arm 130 coupled to the movable platform 215, it should be understood that the movable arms 130 may be configured to move (e.g., translate) relative to the platform 215 in response to movement of the movable platform 215 along the distal body 112C.

Each of the aforementioned devices, assemblies, and methods may be used to facilitate access to a target treatment site and provide enhanced control of ancillary tools/devices (e.g., end effectors) for use at the target treatment site. By providing a medical device with a platform capable of suspending one or more devices for moving a plurality of tools/devices, a user may interact with a target treatment site using the various tools/devices of the medical device during a procedure via with enhanced control and maneuverability by the platform. In this instance, a user may reduce overall procedure time, increase efficiency of procedures, and/or avoid unnecessary harm to a subject's body caused by limited control of the ancillary tools/devices.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:
1. A medical device, comprising:
a body, wherein the body includes a slot;
an arm extending from the body and defining a lumen, wherein the lumen of the arm includes an inlet opening and an outlet opening sized and shaped to receive a first device such that the first device is suspended relative to the body, wherein the arm includes a first end and a second, terminal end, wherein the inlet opening is positioned proximally relative to the outlet opening and is configured to form a seal against the first device, wherein the outlet opening is positioned along a curved portion of the arm, wherein the inlet opening defines the second, terminal end of the arm, and wherein the outlet opening is positioned between the first end of the arm and the second, terminal end of the arm, wherein translation of the arm relative to the body is configured to move the first device relative to the body, wherein the arm includes a curved portion, wherein the slot is configured to receive the first end of the arm such that the arm is movable within the slot; and
a receiver extending from the body and configured to receive a second device such that the second device is suspended relative to the body.

2. The medical device of claim 1, wherein the body includes a locking mechanism engaged with the arm and configured to fix the arm at one of a plurality of positions relative to the body.

3. The medical device of claim 1, wherein the arm is configured to move laterally relative to the body in one or more lateral directions.

4. The medical device of claim 1, wherein the arm is movable independent of the receiver such that the first device is movable relative to the second device.

5. The medical device of claim 1, wherein at least a portion of the arm is transparent such that the lumen of the arm is visible to allow visualization of the first device within the lumen of the arm.

6. The medical device of claim 1, wherein the arm is configured to pivot relative to the body in one or more pivotable directions.

7. The medical device of claim 1, wherein the outlet opening is positioned adjacent to the receiver and is configured to permit the first device to extend outwardly from the arm and toward the second device.

8. The medical device of claim 1, wherein the slot is a first slot, wherein the first slot is formed through a sidewall of the body, and wherein the body further comprises a second slot formed through a top wall of the body, wherein the second slot is configured to receive a locking mechanism, wherein the locking mechanism is configured to engage with the arm to fix the arm at one of a plurality of positions within the first slot.

9. The medical device of claim 1, wherein the outlet opening is formed on an outer surface of the curved portion of the arm.

10. A medical device, comprising:
a platform having a body defined by a proximal end and a distal end, wherein the body includes a slot extending through a sidewall of the body, wherein the slot extends between the proximal end and the distal end of the body;
an arm extending from the body and defining a lumen configured to receive a first device, wherein:
the lumen of the arm includes an inlet opening and an outlet opening each sized and shaped to receive the first device,
the arm includes a curved portion that extends through the slot of the body,
the inlet opening is configured to form a seal against the first device, and the outlet opening is configured to permit the first device to extend outwardly from the arm and toward a second device,
the outlet opening is formed on an outer surface of the curved portion,
the arm extends laterally outward through the slot and is movable within the slot,
the arm is configured to suspend the first device relative to an ancillary surface, and
the first device is movable between the proximal end and the distal end of the body in response to translation of the arm along the slot of the body, and
the outlet opening is formed on an outer surface of the curved portion the outlet opening is formed on an outer surface of the curved portion; and
a receiver at the distal end of the body and configured to suspend a second device relative to the ancillary surface, wherein the second device is fixed at the distal end, and wherein the arm is movable independent of the receiver such that the first device is movable relative to the second device.

11. The medical device of claim 10, wherein the body further includes a clamp configured to secure the platform to an ancillary structure, wherein the clamp includes a pair of jaws, wherein the ancillary structure is received between the pair of jaws.

12. The medical device of claim 11, wherein the clamp further includes a brace, wherein the brace is movable relative to the clamp, wherein the brace extends through one jaw of the pair of jaws.

13. The medical device of claim 11, wherein the clamp is on a proximal end of the body, and wherein the slot is disposed between the receiver and the clamp.

14. A medical device, comprising:
a fixed body;
an arm having a curved portion extending through the fixed body, wherein the arm is movable relative to the fixed body, wherein the arm includes an inlet opening and an outlet opening, wherein the outlet opening is positioned on the curved portion of the arm, wherein the inlet opening defines a terminal end of the arm, wherein each of the inlet opening and the outlet opening is configured to receive a first device, wherein the first device is movable relative to the fixed body in response to translation of the arm relative to the fixed body, and wherein the outlet opening is configured to permit the first device to extend outwardly from the arm and toward a second device; and
a receiver extending from a distal end of the fixed body and configured to receive the second device, wherein the first device is movable relative to the second device.

15. The medical device of claim 14, wherein the outlet opening is formed between a first, proximal end of the arm and a second end of the arm that extends through the fixed body.

* * * * *